(12) United States Patent
Park

(10) Patent No.: US 8,998,612 B2
(45) Date of Patent: Apr. 7, 2015

(54) DENTAL IMPLANT FIXTURE AND IMPLANT SYSTEM HAVING THE SAME

(75) Inventor: Kwang Bum Park, Suseong-gu (KR)

(73) Assignee: Megagen Implant Co, Ltd., Gyeongsangbuk-do (KR)

( * ) Notice: Subject to any disclaimer, the term of this patent is extended or adjusted under 35 U.S.C. 154(b) by 234 days.

(21) Appl. No.: 13/044,890

(22) Filed: Mar. 10, 2011

(65) Prior Publication Data

US 2012/0231419 A1    Sep. 13, 2012

(51) Int. Cl.
*A61C 8/00*      (2006.01)

(52) U.S. Cl.
CPC ..................... *A61C 8/0022* (2013.01)

(58) Field of Classification Search
USPC .................. 433/172–176, 201.1, 67, 18, 19; 606/264, 275, 301–330; 411/411–418
See application file for complete search history.

(56) References Cited

U.S. PATENT DOCUMENTS

| | | | | |
|---|---|---|---|---|
| 5,259,398 A | * | 11/1993 | Vrespa | 128/898 |
| 5,642,996 A | * | 7/1997 | Mochida et al. | 433/174 |
| 6,030,162 A | * | 2/2000 | Huebner | 411/413 |
| 6,217,331 B1 | * | 4/2001 | Rogers et al. | 433/173 |
| 2001/0044095 A1 | * | 11/2001 | Rizzo et al. | 433/173 |
| 2004/0006346 A1 | * | 1/2004 | Holmen et al. | 606/73 |
| 2005/0250074 A1 | * | 11/2005 | Lang et al. | 433/174 |

FOREIGN PATENT DOCUMENTS

| | | |
|---|---|---|
| JP | 08-182759 A | 7/1996 |
| JP | 2003-116969 A | 4/2003 |
| KR | 10-2004-0074877 A | 8/2004 |
| KR | 10-2005-0029482 A | 3/2005 |
| KR | 20-0401027 Y1 | 11/2005 |
| KR | 20-0416306 Y1 | 5/2006 |
| KR | 10-0635973 B1 | 10/2006 |
| KR | 10-2007-0030421 A | 3/2007 |
| KR | 10-2010-0022898 A | 3/2010 |

OTHER PUBLICATIONS

Office Action dated Aug. 12, 2011 in Korean Application No. 10-2011-0028367, filed Mar. 29, 2011.
Office Action dated Oct. 10, 2011 in Korean Application No. 10-2010-0037567, filed Apr. 22, 2010.
Office Action dated Nov. 2, 2011 in Korean Application No. 10-2011-0021544.

* cited by examiner

*Primary Examiner* — Yogesh Patel
(74) *Attorney, Agent, or Firm* — Saliwanchik, Lloyd & Eisenschenk

(57) ABSTRACT

Provided are a dental implant fixture and an implant system including the same. The implant system includes at least two fixtures. The at least two fixtures includes a first fixture including a first body and a first thread part, the first thread part having a spiral shape and disposed on at least a part of an outer surface of the first body; and a second fixture including a second body and a second thread part, the second body having the same shape and standard as those of the first body, the second thread part having a spiral shape and disposed on at least a part of an outer surface of the second body. A diameter of the second thread part is different from a diameter of the first thread part.

8 Claims, 8 Drawing Sheets

DENTAL IMPLANT FIXTURE AND IMPLANT SYSTEM HAVING THE SAME

BACKGROUND

The present disclosure relates to a dental implant fixture and an implant system having the same.

In principle, an implant means a substitute configured to restore damaged human tissue. However, in dentistry, an implant means a series of medical procedures for implanting an artificial tooth.

In the medical procedures, a fixture, which is a dental root formed of such rejection-free material as titanium to replace a damaged dental root, is implanted into an alveolar bone where a tooth was pulled out, and then a dental implant is fixed to restore functions of the tooth.

Typical prostheses or dentures may hurt adjacent teeth and bones with time. However, an implant does not hurt adjacent tooth tissue, and can be used semi-permanently since it causes no tooth decay while having the same function and shape as a natural tooth.

In the medical procedures, also referred to as an implant or implant procedures, a designated drill is used to bore a hole at an implant location, and then a fixture is implanted into and osteointegrated with an alveolar bone, although the procedures may be different depending upon the type of the fixture. Then, in general, an abutment is coupled with the fixture, and a finishing prosthesis is applied to the abutment to finish the procedures.

An implant may restore a single missing tooth, increase the functions of the dentures of a patient with partial or complete anodontia, improve the appearance of a dental prosthesis, disperse the excessive stress upon adjacent supporting bone tissue, and help stabilize a set of teeth.

In general, such an implant includes a fixture which is an artificial dental root to be implanted, an abutment coupled with the fixture, an abutment screw fixing the abutment to the fixture, and an artificial tooth coupled with the abutment. Here, a healing abutment (not shown) may be coupled with the fixture to maintain the coupled state before the abutment is coupled with the fixture, i.e., until the fixture is osteointegrated with an alveolar bone.

A fixture, which is a part of an implant, is implanted into a drilled hole in an alveolar bone where the medical procedures are to be applied, and acts as an artificial dental root. Therefore, a fixture needs to be firmly implanted in the alveolar bone.

Thus, a thread part (thread) may be disposed on the outer surface of a fixture so that the fixture is firmly coupled with the inner sidewall of an alveolar bone where a drilled hole is formed. The thread part is led into the alveolar bone so that the fixture and the alveolar bone are firmly coupled with each other, and strengthens the force with which the fixture fixes the alveolar bone by increasing the contact area of both.

However, a typical dental implant has a limitation that the direction in which a fixture is implanted during the early stage of implanting is difficult to be aligned since the thread part is disposed across the outer surface of the fixture.

Meanwhile, as described above, an implant surgery is carried out by forming a hole with a drill in an alveolar bone, implanting a fixture in the hole, coupling the fixture with an abutment when osteointegration progresses, and then applying an artificial tooth to finish the procedures.

In such an implant surgery, fixtures with different sizes (maximum thread diameters) may be used depending upon operation conditions. Then, different drills need to be used. Usually, a large-scale drill is used for a large fixture, and a small-scale drill is used for a small fixture since the bodies of the fixtures vary depending on the sizes of the fixtures.

However, a cumbersome operation may be entailed when a drill corresponding to the size of a fixture needs to be selected, or when an additional boring is required for implanting a larger fixture with a hole for fixture implanting already formed in an alveolar bone. Especially, when another fixture is implanted after an initial implanting failed, an additional boring with an additional drill is necessary since the sizes of the bodies of the fixtures are different.

Therefore, the development of a new implant system is required for more convenient implant procedures.

BRIEF SUMMARY

Embodiments provide an implant system with which an implant surgery can be conveniently performed because another fixture having a different size can be used without additional drilling when implantation of a first fixture fails.

Embodiments also provide a dental implant fixture with which an implant surgery can be conveniently performed because the direction of initial implantation can be easily guided.

In one embodiment, an implant system including at least two fixtures, wherein the at least two fixtures include: a first fixture including a first body and a first thread part, the first thread part having a spiral shape and disposed on at least a part of an outer surface of the first body; and a second fixture including a second body and a second thread part, the second body having the same shape and standard as those of the first body, the second thread part having a spiral shape and disposed on at least a part of an outer surface of the second body, wherein a diameter of the second thread part is different from a diameter of the first thread part.

The diameter of the second thread part may be greater than the diameter of the first thread part.

Each of the first and second fixtures may further include an entrance guide part extending upward from a bottom side of the body to a predetermined position of the body, so as to guide the body when the body is implanted.

The entrance guide part may include: a flat portion disposed at the bottom side of the body; an inclined portion extending upward from an edge of the flat portion and having an upwardly increasing radius; and a rounded portion connected between the inclined portion and the thread part and rounded toward a vertical axis of the body.

The entrance guide part may be disposed in a non-threaded region where the thread part is not disposed.

The entrance guide part may include: a flat portion disposed at the bottom side of the body; an inclined portion extending upward from an edge of the flat portion and having an upwardly increasing radius; and a rounded portion connected between the inclined portion and the thread part and rounded toward a vertical axis of the body.

Each of the first and second fixtures may include: a taper part having a downwardly decreasing diameter; and a cylinder part extending from a bottom side of the taper part and having a uniform diameter.

Each of the bodies of the first and second fixtures may include: a bevel part at an upper side; at least one cutting edge portion disposed in the thread part and extending downward along a circumferential direction of the body; and an abutment coupling part recessed from a topside of the body to a predetermined depth.

The at least one cutting edge portion may include even number cutting edge portions, and each two of the even number cutting edge portions may be disposed at opposite positions.

The at least one cutting edge portion may include odd number cutting edge portions arranged at regular intervals.

Each of the thread parts may include: a distal end portion which is vertical or inclined to a predetermined side; and a rounded portion disposed at a top or bottom side of the distal end portion to reduce a resistive torque during implantation.

Each of imaginary outlines of the first and second fixtures may include a taper region and a straight region.

Each of the imaginary outlines may include: a first taper region having an upwardly increasing diameter and extending upward from a bottom side of the body; a first straight region extending upward from an end of the first taper region; a second taper region having an upwardly increasing radius and extending upward from an end of the first straight region; and a second straight region extending from an end of the second taper region to a topside of the body.

The implant system may further include a common drill configured to form a drill hole for implanting either the first fixture or the second fixture.

The taper part may include cylinder portions each disposed between ridges of the thread part and having a uniform diameter, wherein one of the cylinder portions disposed at a lower side of a given ridge of the thread part may have a diameter smaller than a diameter of another of the cylinder portions disposed at an upper side of the given ridge of the thread part.

In another embodiment, a dental implant fixture includes: a body; a thread part disposed on at least a part of an outer surface of the body; and an entrance guide part disposed in a non-threaded region of a lower side of the body so as to guide the body when the body is initially implanted, wherein the entrance guide part includes: a flat portion disposed at a bottom side of the body; an inclined portion extending upward from an edge of the flat portion and having an upwardly increasing radius; and a rounded portion connected between the inclined portion and the thread part and rounded toward a vertical axis of the body.

The body may include: a taper part having a downwardly decreasing diameter; and a cylinder part extending from a bottom side of the taper part and having a uniform diameter.

The taper part may include cylinder portions each disposed between ridges of the thread part and having a uniform diameter, wherein one of the cylinder portions disposed at a lower side of a given ridge of the thread part may have a diameter smaller than a diameter of another of the cylinder portions disposed at an upper side of the given ridge of the thread part.

The body may include: a bevel part at an upper side; at least one cutting edge portion disposed in the thread part and extending downward along a circumferential direction of the body; and an abutment coupling part recessed from a topside of the body to a predetermined depth.

The at least one cutting edge portion may include even number cutting edge portions, and each two of the even number cutting edge portions may be disposed at opposite positions.

The at least one cutting edge portion may include odd number cutting edge portions arranged at regular intervals.

The thread part may include: a distal end portion 131 which is vertical or inclined to a predetermined side; and a rounded portion disposed at a top or bottom side of the distal end portion to reduce a resistive torque during implantation.

The imaginary outline may include: a first taper region having an upwardly increasing diameter and extending upward from a bottom side of the body; a first straight region extending upward from an end of the first taper region; a second taper region having an upwardly increasing radius and extending upward from an end of the first straight region; and a second straight region extending from an end of the second taper region to a topside of the body.

According to the embodiments, although implantation of the first fixture fails, the second fixture can be directly implanted without additional drilling. Therefore, an implant surgery can be performed more easily as compared with the related art.

In addition, according to the embodiments, since the direction of initial implantation can be easily guided, an implant surgery can be performed more conveniently.

The details of one or more embodiments are set forth in the accompanying drawings and the description below. Other features will be apparent from the description and drawings, and from the claims.

DETAILED DESCRIPTION

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
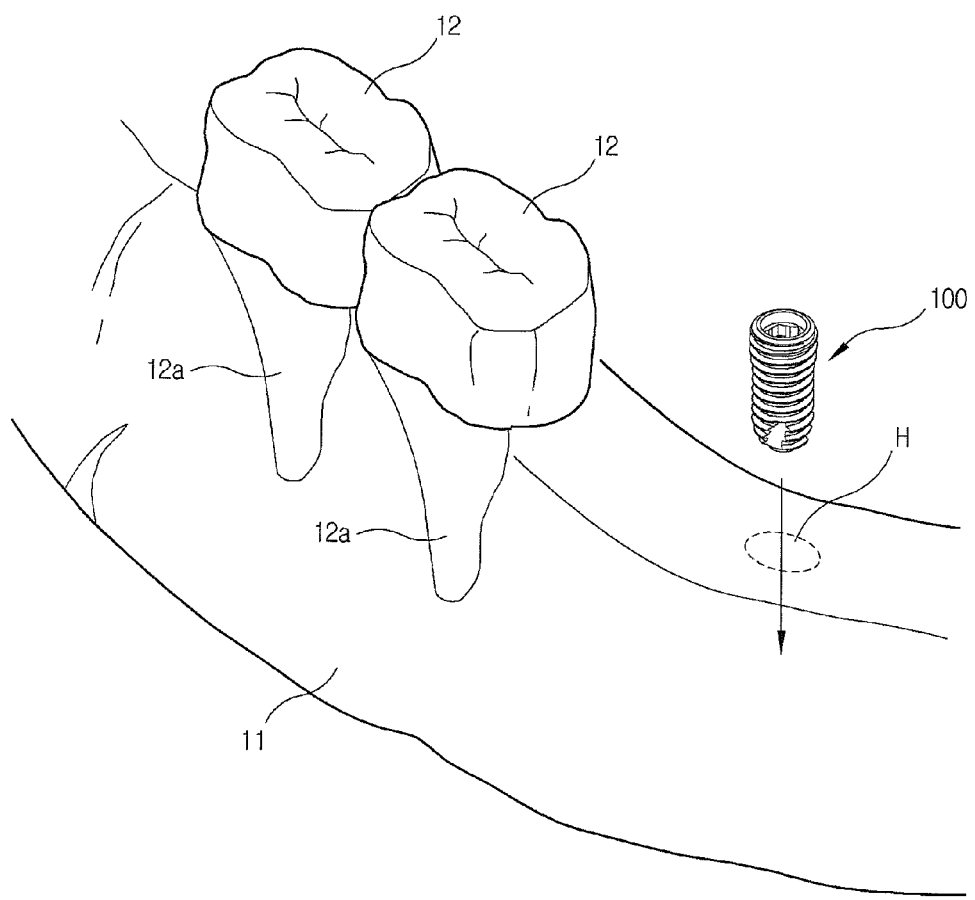
FIG. 1 is a schematic view illustrating implantation of a dental implant fixture according to an embodiment.

FIG. 1 is a schematic view illustrating implantation of a dental implant fixture according to an embodiment.

Referring to FIG. 1, a plurality of teeth 12 are arranged along a gum 11. The teeth 12 are primary digestive means that break food into small pieces before the food is sent to the stomach. Usually, people have twenty eight teeth.

If one of the teeth 12 is lost (for example, a molar is lost), it is not good for the appearance, as well as it is difficult to chew.

Thus, a first fixture 100 may be implanted in the gum 11 as a substitute for a dental root 12a of the lost tooth 12. If the size of the first fixture 100 is not suitable, a second fixture 200 (refer to FIG. 8) may be implanted. The first fixture 100 and the second fixture 200 may be formed of titanium (Ti) or a titanium (Ti) alloy that the human body does not reject.

In this way, the first fixture 100 or the second fixture 200 may be implanted in an alveolar bone inside the gum 11. Before the implantation of the first fixture 100, drilling is carried out. That is a drill hole (H) is formed in the alveolar bone at a predetermined position.

Figure 2:
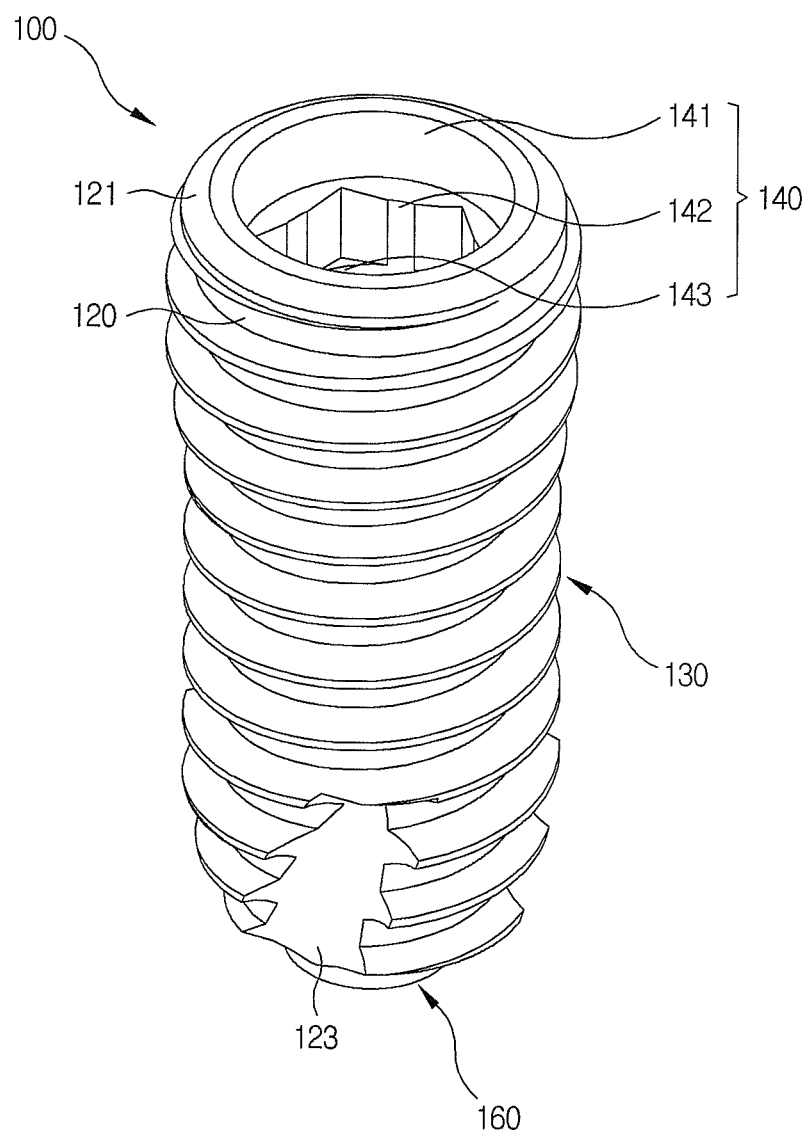
FIG. 2 is a perspective view illustrating a first fixture according to an embodiment.
Figure 3:
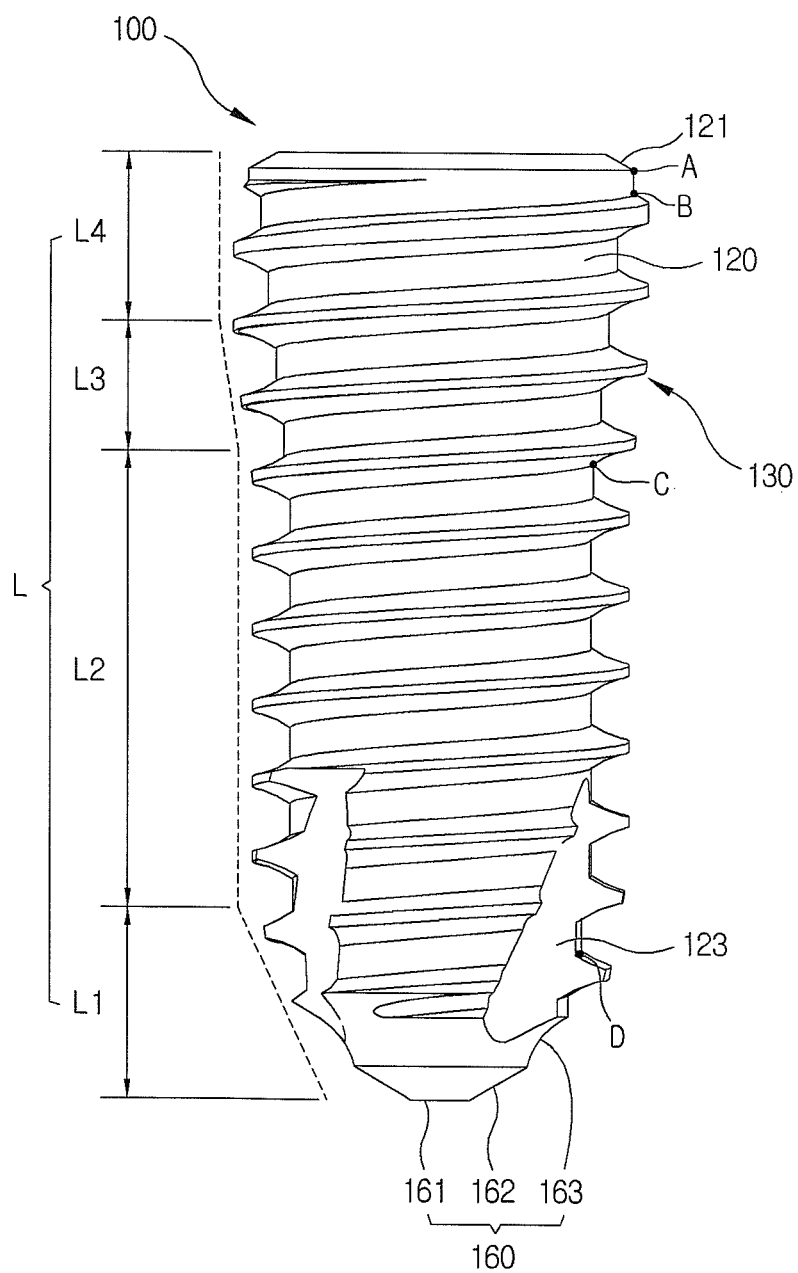
FIG. 3 is a side view illustrating the first fixture according to an embodiment.
Figure 4:
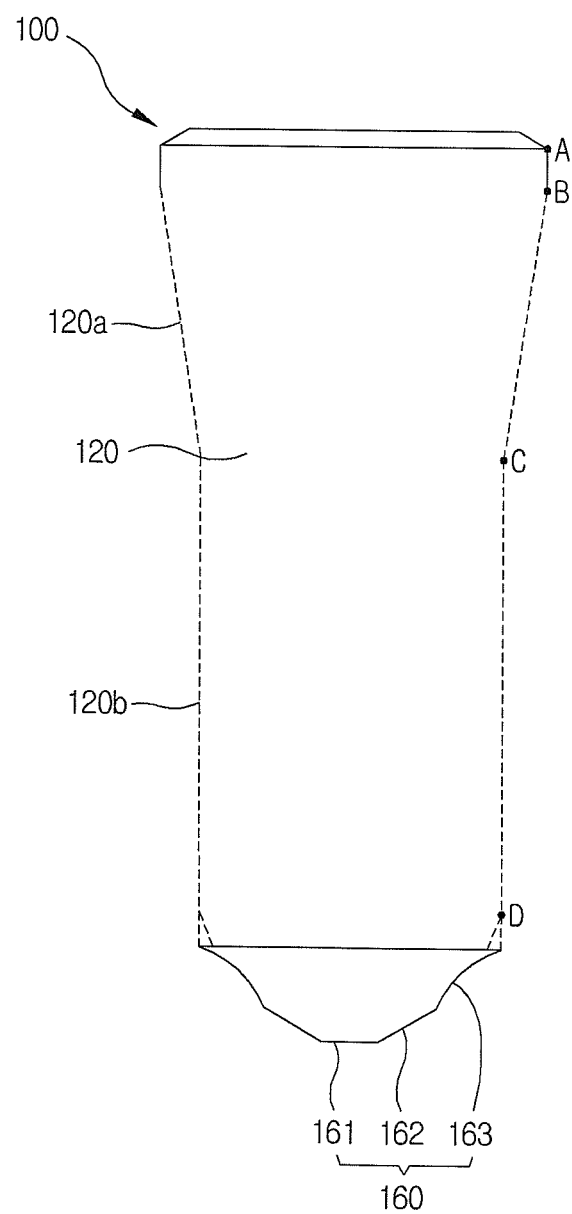
FIG. 4 is a schematic view illustrating the contour of a body of the first fixture according to an embodiment.
Figure 5:
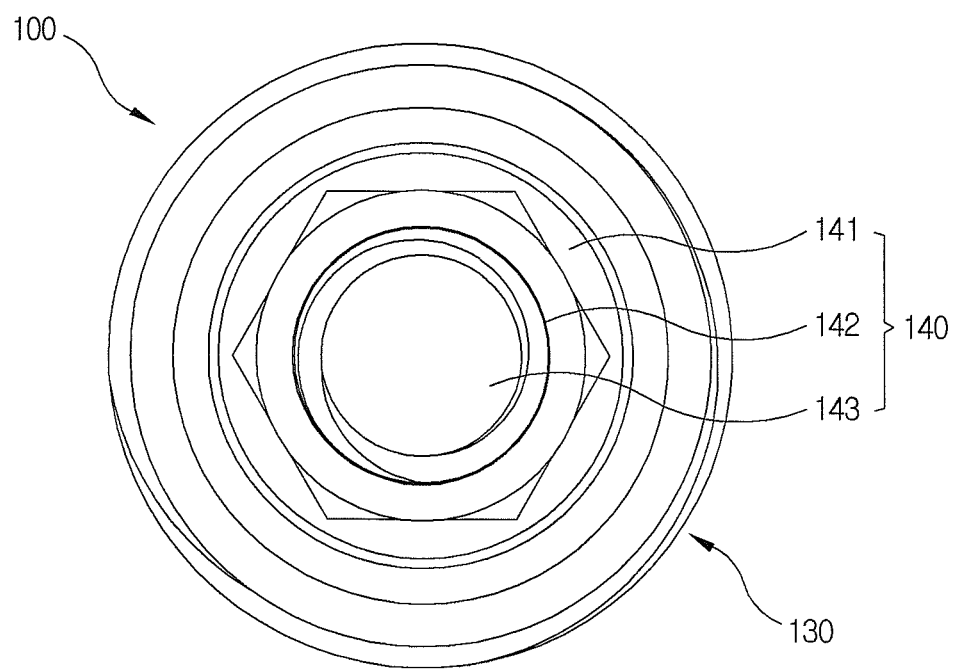
FIG. 5 is a plan view illustrating the first fixture according to an embodiment.
Figure 6:
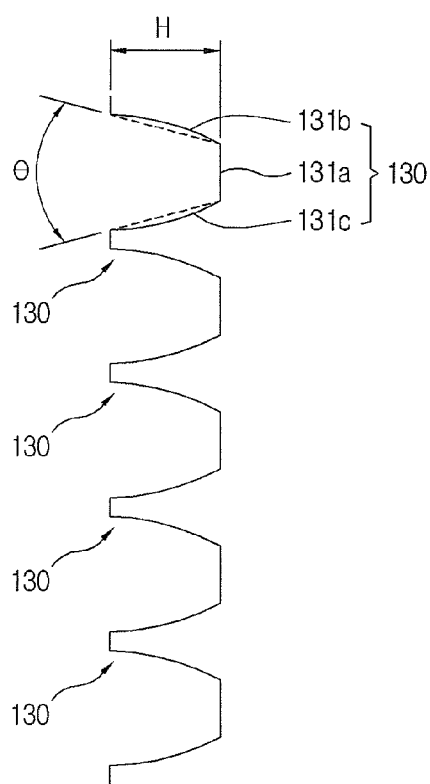
FIG. 6 is a partial enlarged view illustrating a thread part of the first fixture according to an embodiment.
Figure 7:
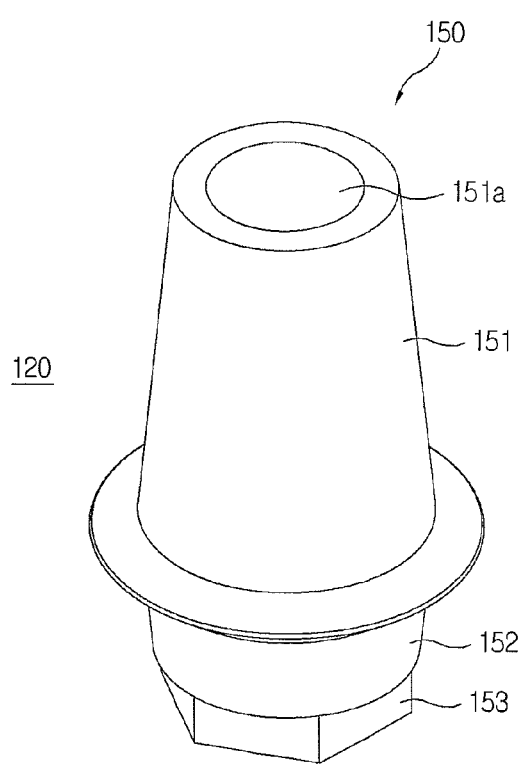
FIG. 7 is a perspective view illustrating an abutment to be coupled to the first fixture according to an embodiment.

FIG. 2 is a perspective view illustrating the first fixture 100 according to an embodiment; FIG. 3 is a side view illustrating the first fixture 100 according to an embodiment; FIG. 4 is a schematic view illustrating a body contour of the first fixture 100 according to an embodiment; FIG. 5 is a plan view illustrating the first fixture 100 according to an embodiment; FIG. 6 is a partial enlarged view illustrating a thread part of the first fixture 100 according to an embodiment; and FIG. 7 is a perspective view illustrating an abutment to be coupled to the first fixture 100 according to an embodiment.

As shown in FIGS. 2 to 6, the first fixture 100 of the current embodiment includes: a body 120; a thread part 130 disposed on at least a part of the outside of the body 120 in a spiral shape; and an entrance guide part 160 disposed from the bottom of the body 120 to a predetermined upper part of the body 120 to guide the body 120 when the body 120 is initially implanted.

In detail, the body 120 constitutes a central stem of the first fixture 100. Since the first fixture 100 is implanted in the direction of an arrow of FIG. 1, at least a part of the outside of the body 120 is tapered in a manner such that the diameter of the part reduces downward.

In the related art, a body of a fixture (not shown) has a cylindrical shape having a uniform diameter. However, in the current embodiment, the body 120 of the first fixture 100 is partially tapered in a manner such that the diameter of the body 120 reduces from an upper part to a lower part of the body 120.

As shown in FIG. 4, the body 120 includes a taper part 120a and a cylinder part 120b. The taper part 120a is tapered in a manner such that the diameter of the taper part 120a reduces from a position close to the topside of the first fixture 100 to a position spaced a predetermined distance from the topside of the first fixture 100. The cylinder part 120b extends from the taper part 120a to a position close to the bottom side of the body 120 and has a uniform diameter.

As shown in the drawings, the diameter of a vertical section of the taper part 120a of the body 120 may be reduced in the form of a stair. That is, in regions A to C, the outer diameter of a part of the body 120 is constant from the bottom surface of a ridge of a thread to the top surface of the neighboring ridge of the thread. However, the diameter of the body 120 at the bottom surface of the neighboring ridge of the thread is smaller than the diameter of the body 120 at the top surface of the neighboring ridge of the thread.

Alternatively, in the regions A to C, the body 120 may be tapered in a manner such that the vertical section of the body 120 is linearly reduced.

The cylinder part 120b facilitates initial implantation of the first fixture 100, and the taper part 120a makes it possible to fix the first fixture 100 more securely. Therefore, according to the current embodiment, implantation and fixation can be carried out more efficiently as compared with the related art. In the latter case, the taper part 120a may have a slope angle of about 10 degrees to 60 degrees. For example, the slope angle of the taper part 120a may be 30 degrees in the current embodiment. However, the scope of the present disclosure is not limited thereto.

A bevel part 121 is disposed at the edge of the topside of the body 120. The bevel part 121 has a sloped surface to increase the contact area with an alveolar bone and thus to increase a fixing force. In addition, since the diameter of the bevel part 121 reduces upward, the first fixture 100 may not be easily detached from an alveolar bone.

Cutting edge portions 123 is disposed in a lower region of the thread part 130 of the body 120. The cutting edge portions 123 are formed in the thread part 130 along the circumference of the body 120. Owing to sharp edges of the cutting edge portions 123, the first fixture 100 may be implanted more easily.

The cutting edge portions 123 may be formed in the thread part 130 at an angle from the length direction of the body 120. In this case, the cutting edge portions 123 may be arranged at opposite positions along the outer circumference of the body 120. That is, each two of even number cutting edge portions 123 may be disposed at opposite positions. However, the scope of the present disclosure is not limited thereto. For example, the cutting edge portions 123 may be arranged along the outer circumference of the body 120 not at opposite positions. That is, odd number cutting edge portions 123 may be arranged at regular intervals, and imaginary lines connecting the cutting edge portions 123 may form a regular triangle, a regular pentagon, etc.

Referring to FIGS. 2 and 5, an abutment coupling part 140 is disposed in the topside of the body 120 for coupling with an abutment 150 (refer to FIG. 7).

With reference to FIG. 7, the abutment 150 will now be described briefly. The abutment 150 has a truncated cone shape. The abutment 150 includes an abutment body 151 through which a penetration hole 151a is formed, a first coupling part 152 disposed at a lower side of the abutment body 151, and a second coupling part 153 disposed at a lower side of the first coupling part 152.

The first coupling part 152 may be fitted into a first recessed part 141 (described later) of the abutment coupling part 140, and the second coupling part 153 may be fitted into a second recessed part 142 (described later) of the abutment coupling part 140.

Since the first recessed part 141 has a tapered inner wall, the outer surface of the first coupling part 152 of the abutment 150 is also tapered. The second coupling part 153 has a shape corresponding to the shape of the second recessed part 142.

In detail, the abutment coupling part 140 includes the first recessed part 141, the second recessed part 142, and a screw hole 143. The first recessed part 141 is recessed from the topside of the body 120 in the length direction of the body 120. The second recess 142 is secondarily recessed from the bottom of the first recessed part 141 in the length direction of the body 120 and has a hexagon shape. The screw hole 143 is formed in a center region of the second recessed part 142 in the length direction of the second recessed part 142. An abutment screw (not shown) is coupled to the screw hole 143 for coupling the abutment 150 to the abutment coupling part 140.

The first recessed part 141 is coupled with the first coupling part 152 of the abutment 150 (refer to FIG. 7). At this time, it may be necessary to bring the first coupling part 152 of the abutment 150 into tight contact with the first recessed part 141 of the first fixture 100. This is to prevent detachment and guarantee sealing for avoiding infection. The inner wall of the first recessed part 141 is tapered downwardly so that the diameter of the inner wall decreases from the upper side to the lower side. Like the inclined angle of the outer surface of the first coupling part 152 of the abutment 150, the inclined angle of the inner wall of the first recessed part 141 may be in the range from 2 degrees to 6 degrees. If the inclined angle of the inner wall of the first recessed part 141 is in the above-mentioned angle range, when the abutment 150 is coupled to the first fixture 100, the first coupling part 152 of the abutment 150 can be securely or tightly coupled to the to the first recessed part 141.

The second coupling part 153 of the abutment 150 passes through the first recessed part 141 and is coupled to the second recessed part 142. As shown in FIG. 7, if the second coupling part 153 of the abutment 150 has a hexagonal nut shape, the second recessed part 142 may also be formed into a hexagonal shape. That is, the second recessed part 142 has a polygonal shape including a hexagonal shape, and the second coupling part 153 of the abutment 150 has a polygonal shape corresponding to the shape of the second recessed part 142. Therefore, after the second coupling part 153 is inserted in the second recessed part 142, the abutment 150 is not rotated.

After the first coupling part 152 and the second coupling part 153 of the abutment 150 are respectively inserted in the first recessed part 141 and the second recessed part 142 of the abutment coupling part 140, an abutment screw (not shown) is inserted in the penetration hole 151a of the abutment 150 and is coupled to the screw hole 143 of the abutment coupling part 140. The screw hole 143 has the same size as the penetration hole 151a of the abutment 150.

The thread part 130 is formed on at least a part of the outer surface of the body 120 and is coupled to an inner surface of the drill hole (H) (refer to FIG. 1). In other words, when the first fixture 100 is inserted in the drill hole (H) while being rotated, the thread part 130 burrows into the inner surface of the drill hole (H). Unlike a fixture of the related art, the thread part 130 of the current embodiment is not formed on the entire region of the outer surface of the body 120 but the thread part 130 is formed on the other region of the outer surface of the body 120 except for the entrance guide part 160.

The shape or structure of the thread part 130 will now be explained. Referring to FIG. 6, the thread part 130 includes a vertical or inclined distal end portion 131a, an upper rounded portion 131b forming a top surface of the distal end portion 131a, and a lower rounded portion 131c forming a bottom surface of the distal end portion 131a.

In detail, the shape of the thread of the thread part 130, that is, the shape of the thread part 130 is different from the shape of a general triangular or rectangular thread. That is, the top and bottom surfaces of the distal end portion 131a are not straight but convex.

That is, as shown in FIG. 6, the distal end portion 131a is substantially vertical and straight, and the upper rounded portion 131b and the lower rounded portion 131c which form the top and bottom surfaces of the distal end portion 131a are upwardly and downwardly convex. Only one of the upper rounded portion 131b and the lower rounded portion 131c may be convex. However, in the current embodiment, both the upper rounded portion 131b and the lower rounded portion 131c are symmetrically convex with respect to the distal end portion 131a. In this case, when the first fixture 100 is implanted, resistive torque may be reduced, and thus the first fixture 100 may be easily implanted.

For example, an angle θ between lines drawn from distal ends to proximal ends of the upper and lower rounded portions 131b and 131c (refer to dashed lines in FIG. 6) may be about 30 degrees. However, the scope of the present disclosure is not limited thereto. As described above, the upper and lower rounded portions 131b and 131c are symmetric. However, alternatively, the upper and lower rounded portions 131b and 131c may be asymmetric. In other words, as long as the upper and lower rounded portions 131b and 131c can reduce resistive torque when the first fixture 100 is implanted, the angle between the upper and lower rounded portions 131b and 131c and the symmetric or asymmetric structure may be varied.

Referring to FIGS. 3 and 4, the entrance guide part 160 is formed from the bottom side of the body 120 to a predetermined upper position of the body 120 to guide an insertion direction when the body 120 is initially implanted.

If the entrance guide part 160 is not formed like in the related art, that is, if the thread part 130 is formed even on the entrance guide part 160, it may be difficult to initially insert the body 120 due to the thread part 130. However, according to the current embodiment, at least the entrance guide part 160 where the thread part 130 is not formed can be freely inserted into the drill hole (H), and thus the implantation direction can be properly kept without distortion. Then, the first fixture 100 can be implanted by using the thread part 130. Therefore, implantation can be easily performed.

As described above, the entrance guide part 160 is a non-threaded region formed from the bottom side of the body to a predetermined position of the body 120. The entrance guide part 160 (non-threaded region) may be formed as a part of the first fixture 100 when the first fixture 100 is fabricated, or may be formed through a later process after the thread part 130 is formed on the entire region of the outer surface of the body 120. The entrance guide part 160 may be formed from the bottom side of the body 120 to a position of the body 120 spaced upward from the bottom side of the body 120 by 1 mm to 3 mm.

The entrance guide part 160 includes a flat portion 161 which is horizontal flat, an inclined portion 162 extending upward from the flat portion 161 with an upwardly increasing radius, and a rounded portion 163 connected the inclined portion 162 and the thread part 130 and rounded toward the centerline of the first fixture 100. Unlike that shown in FIG. 4, the rounded portion 163 and the inclined portion 162 together form an arc line.

The overall outer shape of the first fixture 100 will now be described. An imaginary outline (L) of the first fixture 100 drawn from the entrance guide part 160 to the upper end of the thread part 130 is not simply straight but includes a taper region and a straight region. The imaginary outline line (L) may connect distal ends of the ridges of the thread of the thread part 130. The taper region and the straight region may be repeated. This will now be explained.

Referring to FIG. 3, the imaginary outline (L) of the first fixture 100 includes: a first taper region L1 inclined outward and extending upward from the bottom side of the body 120; a first straight region L2 extending upward from an end of the first taper region L1 and having a predetermined length; a second taper region L3 inclined outward and extending upward from an end of the first straight region L2; and a second straight region L3 extending from an end of the second taper region L3 to the topside of the body 120.

As described above, since the imaginary outline (L) of the first fixture 100 includes the first taper region L1, the first straight region L2, the second taper region L3, and the second straight region L4, the following effects may be attained as compared with a straight type fixture (not shown) of the related art.

Since the first fixture 100 can be osseointegrated in a state where a more area of the first fixture 100 makes contact with an alveolar bone, although the size or quality of the alveolar bone is insufficient, the initial fixing force can be increased as compared with the related art when the first fixture 100 is implanted in a drill hole (H) formed in the alveolar bone.

Figure 8:
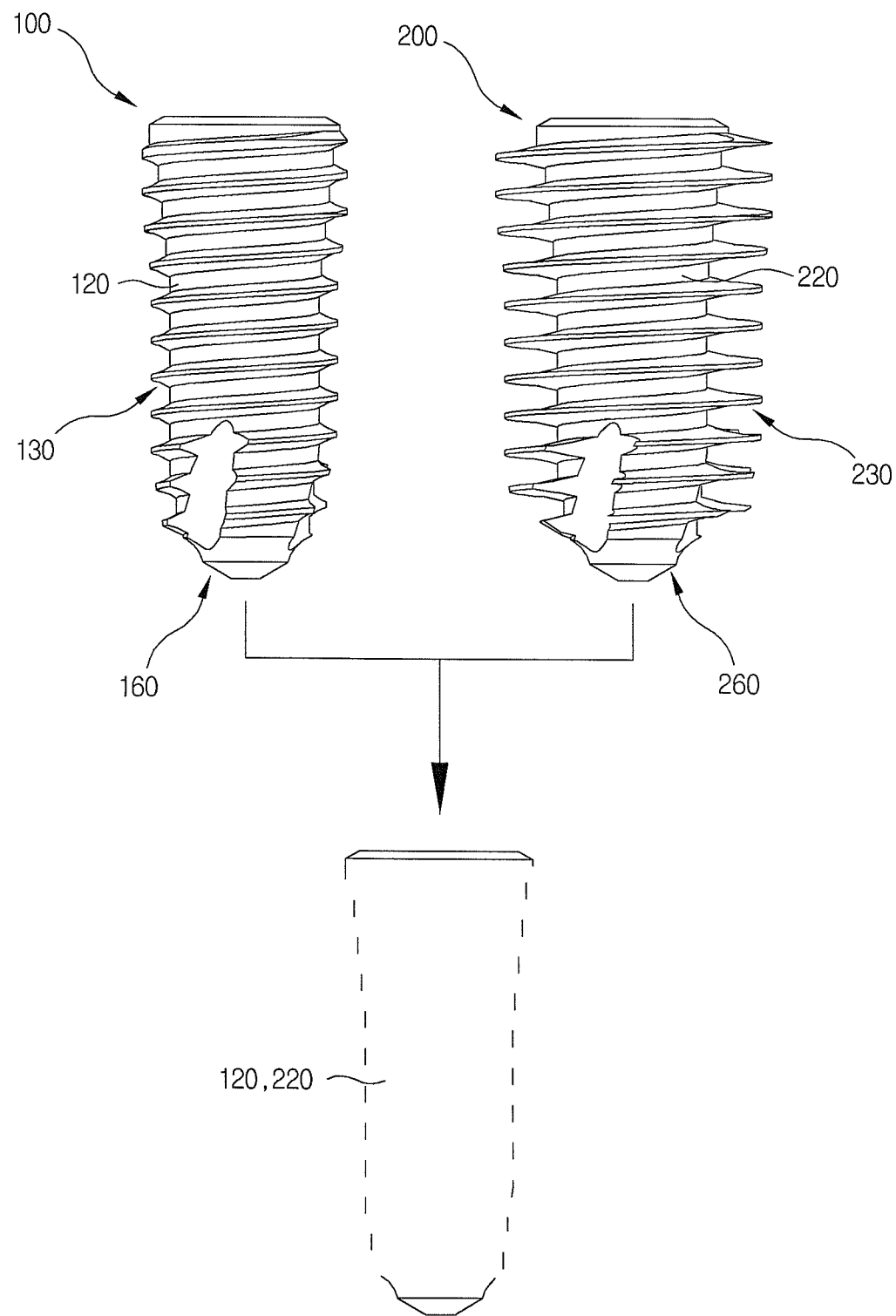
FIG. 8 is a view illustrating an implant system according to an embodiment.
Figure 9:
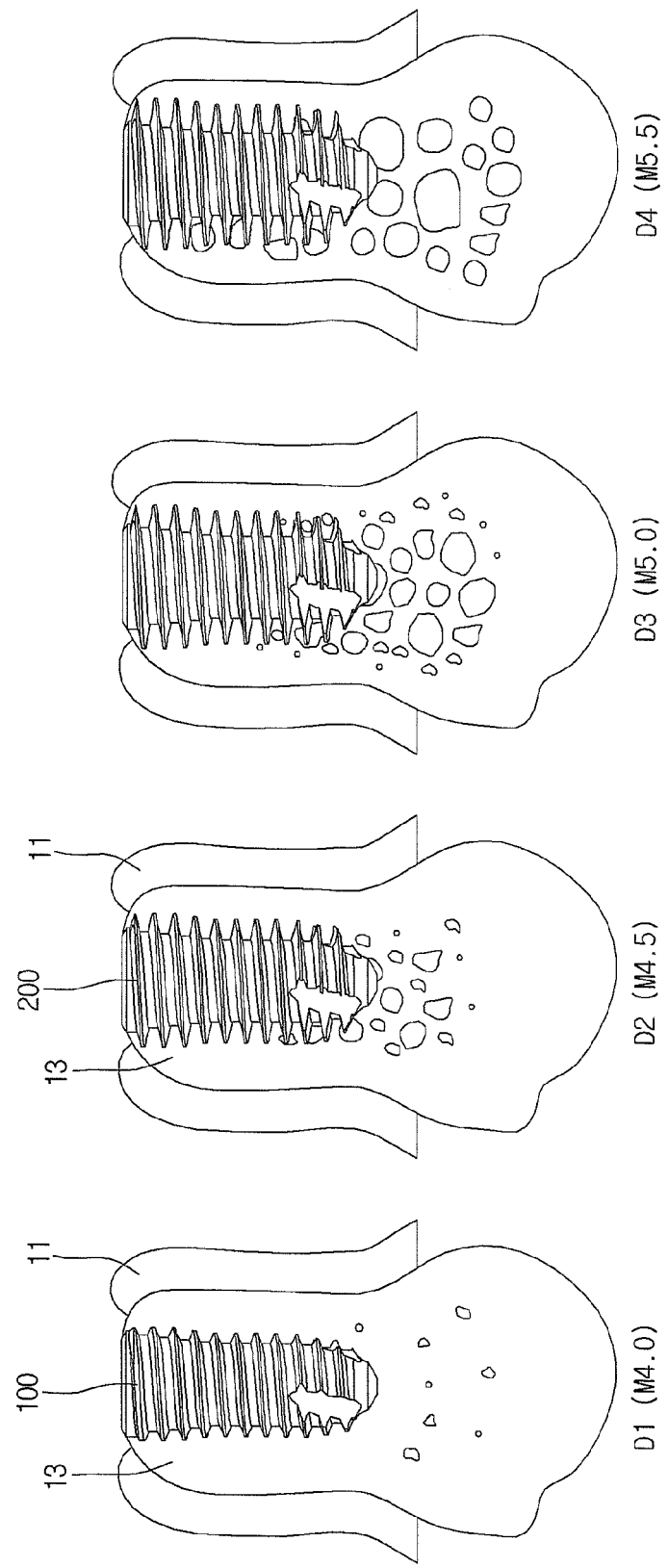
FIG. 9 is a view illustrating four fixtures of different sizes placed in a hole (H) of an alveolar bone.

FIG. 8 is a view illustrating an implant system according to an embodiment, and FIG. 9 is a view illustrating four fixtures of different sizes placed in a hole (H) of an alveolar bone.

Referring to FIGS. 8 and 9, the implant system of the current embodiment includes a plurality of fixtures. Bodies (cores) of the fixtures have the same vertical sectional shape. However, threads of the fixtures have different heights. Hereinafter, two of the fixtures will be described as examples.

The implant system of the current embodiment may include: the above-described first fixture 100; and a second fixture 200 having the same body shape as that of the first fixture 100 but having a thread height different from that of the first fixture 100. Since vertical sectional shapes of cores of the first and second fixtures 100 and 200 are equal, the second fixture 200 can be implanted to a hole where the first fixture 100 was coupled and removed.

Like the first fixture 100, the second fixture 200 includes a second body 220, a second thread part 230, and a second entrance guide part 260. Since the second fixture 200 is similar to the above-described first fixture 100, a detailed description of the second fixture 200 will be omitted.

The second body (second core) 220 of the second fixture 200 have the same shape and size as the first body (first core) 120 of the first fixture 100. However, the width of the second thread part 230 of the second fixture 200 is greater than the width of the first thread part 130 of the first fixture 100.

Since the second thread part 230 of the second fixture 200 is wider than the first thread part 130 of the first fixture 100, the outer diameter of the second fixture 200 is greater than the outer diameter of the first fixture 100. Although the first and second fixtures 100 and 200 have different outer diameters, since the first and second body 100 and 200 of the first and second fixtures 100 and 200 are equal, either the first fixture 100 or the second fixture 200 can be implanted in a hole (H) drilled in an alveolar bone by using the same drill (not shown).

For example, when the first fixture 100 is implanted in a hole (H) formed in an alveolar bone using a common drill as shown in FIG. 1, although implantation of the first fixture 100 fails, the second fixture 200 can be directly implanted in the same hole (H) without having to enlarge the hole (H) or form another hole. Therefore, dental implantation can be easily performed as compared with the related art. This is possible since the first body 120 of the first fixture 100 is equal to the second body 220 of the second fixture 200. However, since the radius of the second thread part 230 of the second fixture 200 is greater than the radius of the first thread part 130 of the first fixture 100, when the second fixture 200 is implanted, the second thread part 230 can burrow into the inner surface of the hole (H) in radial directions as much as the radius difference. Therefore, although the second fixture 200 is implanted in the existing hole (H) without additional drilling, the second fixture 200 may not wobble or fall out.

Referring to FIG. 9, for example, when the first fixture 100 having a thread diameter of 4.0 mm is implanted in a hole (H) formed in an alveolar bone 13 with a common drill, although implantation of the first fixture 100 fails, the second fixture 200 having a thread diameter of 4.5 mm may be implanted in the same hole (H) without additional drilling. In addition, if implantation of the second fixture 200 fails, a third or fourth fixture having a thread diameter of 5.0 mm or 5.5 mm may be implanted in the same hole (H).

This is possible since the first and second bodies 120 and 220 of the first and second fixtures 100 and 200 are equal and the first and second thread parts 130 and 230 have different widths. This may be equal in the cases of other fixtures such as third, fourth, and fifth fixtures.

Based on the above description, an exemplary implant surgery will now be explained.

First, a drill hole (H) is formed in an implantation position of an alveolar bone 13 by using a common drill (not shown). At this time, the diameter of the drill hole (H) may be similar or equal to a maximum width of the body 120.

Next, the first fixture 100 is placed toward the implantation position and inserted into the drill hole (H) of the alveolar bone 13.

When the first fixture 100 is inserted in the drill hole (H), since the entrance guide part 160 of the first fixture 100 can be smoothly inserted in the drill hole (H), the insertion direction of the first fixture 100 may not be distorted. In other words, since the direction of initial implantation can be easily guided, the implant surgery may be performed more easily and conveniently.

After the direction of implantation is fixed by the entrance guide part 160, the first fixture 100 is implanted while being rotated. Then, the first thread part 130 burrows into the inner surface of the drill hole (H) of the alveolar bone 13 in horizontal directions crossing the length direction of the drill hole (H). As a result, a helical groove having the same pitch as the first thread part 130 is formed in the inner surface of the drill hole (H). Therefore, after the implantation, the first fixture 100 can be securely fixed to the alveolar bone 13. Accordingly, the first fixture 100 may not wobble and rapidly osseointegrated.

However, in some cases, implantation of the first fixture 100 may fail. In this case, the second fixture 200 can be directly implanted in the drill hole (H) without additional drilling. As described above, this is possible since the first and second bodies 120 and 220 of the first and second fixtures 100 and 200 are equal.

If the first fixture 100 is successfully implanted, after osseointegration of the first fixture 100, the abutment 150 (refer to FIG. 5) is coupled to the abutment coupling part 140 of the first fixture 100. Osseointegration may proceed as follows. Since the diameter of the drill hole (H) corresponds to the maximum width of the body 120 of the first fixture 100, a space or gap may be formed between lower regions of the outer surface of the body 120 and the inner surface of the drill hole (H). The space or gap is filled as the alveolar bone 13 grows. This process may be defined as osseointegration.

When the abutment 150 is coupled to the abutment coupling part 140, the first coupling part 152 and the second coupling part 153 of the abutment 150 are inserted into and coupled to the first recessed part 141 and the second recessed part 142 of the abutment coupling part 140, respectively. Then, rotation of the abutment 150 is prevented by the coupling between the second coupling part 153 of the abutment 150 and the second recessed part 142 of the abutment coupling part 140. In addition, owing to strong or tight coupling between the first coupling part 152 of the abutment 150 and the first recessed part 141 of the abutment coupling part 140, the abutment 150 may not be easily detached, and the possibility of infection may be reduced owing to reliable sealing formed by the strong or tight coupling.

After the first coupling part 152 and the second coupling part 153 of the abutment 150 are respectively inserted in the first recessed part 141 and the second recessed part 142 of the abutment coupling part 140, an abutment screw (not shown) is inserted in the penetration hole 151a of the abutment 150 and is coupled to the screw hole 143 of the abutment coupling part 140. Then, the implant surgery is completed by attaching a prosthesis to the abutment 150.

As described above, according to the implant system of the current embodiment, although implantation of the first fixture 100 fails, the second fixture 200 can be directly implanted without additional drilling. Therefore, dental implantation can be conveniently performed as compared with the related art.

In addition, the direction of initial implantation can be easily guided when using the first or second dental implant fixture 100 or 200 of the embodiment. Dental implantation can be performed more conveniently.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An implant system configured to be inserted into a patient's mouth/jawbone, comprising at least two fixtures, wherein the at least two fixtures comprise: a first fixture comprising: a first body, a first thread part having a spiral shape and disposed on at least a part of an outer surface of the first body; and a first entrance guide part extending upward from a bottom side of the first body to a predetermined position of the first body to guide the first body when the first body is implanted; and a second fixture comprising: a second body having a same diameter as the first body, a second thread part having a spiral shape and disposed on at least a part of an outer surface of the second body; and a second entrance guide part extending upward from a bottom side of the second body to a predetermined position of the second body to guide the second body when the second body is implanted, wherein an imaginary outline drawn along an outer edge of the thread part of each of the first and second fixtures comprises a taper region and a straight region; wherein a width of the second thread part is different from a width of the first thread part; and wherein a thread height of the second thread part is different from a thread height of the first thread part, wherein the first entrance guide part and the second entrance guide part each comprises: a flat portion disposed at the bottom side of the body; an inclined portion extending upward from an edge of the flat portion and having an upwardly increasing radius; and a thread-free rounded portion connected between the inclined portion and the thread part and rounded toward a vertical axis of the body.

2. The implant system according to claim 1, wherein the width of the second thread part is greater than the width of the first thread part.

3. The implant system according to claim 1, wherein the first entrance guide part and the second entrance guide part each is disposed in a non-threaded region where the thread part is not disposed.

4. The implant system according to claim 1, wherein the first and second fixtures each further comprises:
a bevel part at an upper side;
at least one cutting edge portion disposed in the thread part and extending downward along a circumferential direction of the body; and
an abutment coupling part recessed from a topside of the body to a predetermined depth.

5. The implant system according to claim 1, wherein each of the first and second thread parts comprises: a distal end portion which forms a tip of the thread part and is vertical; and the rounded portion adapted to reduce a resistive torque during implantation.

6. The implant system according to claim 1, wherein each of the imaginary outlines comprises:
a first taper region having an upwardly increasing diameter and extending upward from the bottom side of the body;
a first straight region extending upward from an end of the first taper region;
a second taper region having an upwardly increasing radius and extending upward from an end of the first straight region; and
a second straight region extending from an end of the second taper region to a topside of the body.

7. The implant system according to claim 1, further comprising a common drill configured to form a drill hole for implanting either the first fixture or the second fixture.

8. The implant system according to claim 1, wherein for each of the first and second fixtures, the taper region comprises cylinder portions, each cylinder portion disposed between ridges of the thread part,
wherein one of the cylinder portions disposed at a lower side of a given ridge of the thread part has a diameter smaller than a diameter of another of the cylinder portions disposed at an upper side of the given ridge of the thread part.

* * * * *